(12) United States Patent
Nakanishi et al.

(10) Patent No.: US 9,383,321 B2
(45) Date of Patent: Jul. 5, 2016

(54) INSPECTION APPARATUS AND INSPECTION METHOD

(71) Applicants: DAINIPPON SCREEN MFG. CO., LTD., Kyoto-shi, Kyoto (JP); OSAKA UNIVERSITY, Suita-shi, Osaka (JP)

(72) Inventors: Hidetoshi Nakanishi, Kyoto (JP); Akira Ito, Kyoto (JP); Iwao Kawayama, Suita (JP); Masayoshi Tonouchi, Suita (JP)

(73) Assignees: SCREEN HOLDINGS CO., LTD., Kyoto (JP); OSAKA UNIVERSITY, Osaka (JP)

( * ) Notice: Subject to any disclaimer, the term of this patent is extended or adjusted under 35 U.S.C. 154(b) by 0 days.

(21) Appl. No.: 14/465,435

(22) Filed: Aug. 21, 2014

(65) Prior Publication Data

US 2015/0053869 A1 Feb. 26, 2015

(30) Foreign Application Priority Data

Aug. 23, 2013 (JP) .................................. 2013-173140

(51) Int. Cl.
*G01N 21/64* (2006.01)

(52) U.S. Cl.
CPC ........ *G01N 21/6489* (2013.01); *G01N 21/6456* (2013.01); *G01N 2021/6417* (2013.01); *G01N 2201/10* (2013.01)

(58) Field of Classification Search
CPC .................................................. G01N 21/6489
See application file for complete search history.

(56) References Cited

U.S. PATENT DOCUMENTS

| 7,852,102 | B2* | 12/2010 | Kitagawa | G01R 31/311 324/754.23 |
|---|---|---|---|---|
| 8,129,683 | B2* | 3/2012 | Itsuji | G01N 21/3581 250/341.1 |
| 8,629,411 | B2* | 1/2014 | Beck | G01N 21/6489 250/458.1 |
| 2004/0056648 | A1* | 3/2004 | Matsuyama | H02S 50/10 324/96 |
| 2007/0048884 | A1* | 3/2007 | Nagel | G01N 21/6489 438/16 |
| 2007/0076106 | A1* | 4/2007 | Kamon | H04N 5/2178 348/294 |
| 2011/0216312 | A1* | 9/2011 | Matsumoto | G01N 21/9501 356/237.1 |
| 2012/0012756 | A1* | 1/2012 | Beck | G01N 21/6489 250/459.1 |
| 2013/0043405 | A1* | 2/2013 | Maxwell | G01N 21/6489 250/459.1 |

FOREIGN PATENT DOCUMENTS

| EP | 2546634 A1 | 1/2013 |
|---|---|---|
| GB | 2231958 A | 11/1990 |
| JP | 2009-175127 A | 8/2009 |
| JP | 2013-19861 A | 1/2013 |

OTHER PUBLICATIONS

European Search Report EP Application No. 14181337.5 dated Jan. 13, 2015.

* cited by examiner

*Primary Examiner* — David Porta
*Assistant Examiner* — Djura Malevic
(74) *Attorney, Agent, or Firm* — McDermott Will & Emery LLP

(57) ABSTRACT

An inspection apparatus is an apparatus for inspecting a solar cell panel. The inspection apparatus includes: an excitation light irradiation part for irradiating the solar cell panel with pulsed light for causing the solar cell panel to radiate an electromagnetic wave pulse; a detection part for detecting the electromagnetic wave pulse radiated from the solar cell panel in response to irradiation with the pulsed light; and a temperature changing part for changing a temperature of the solar cell panel at a part irradiated with the pulsed light.

5 Claims, 14 Drawing Sheets

F I G. 2
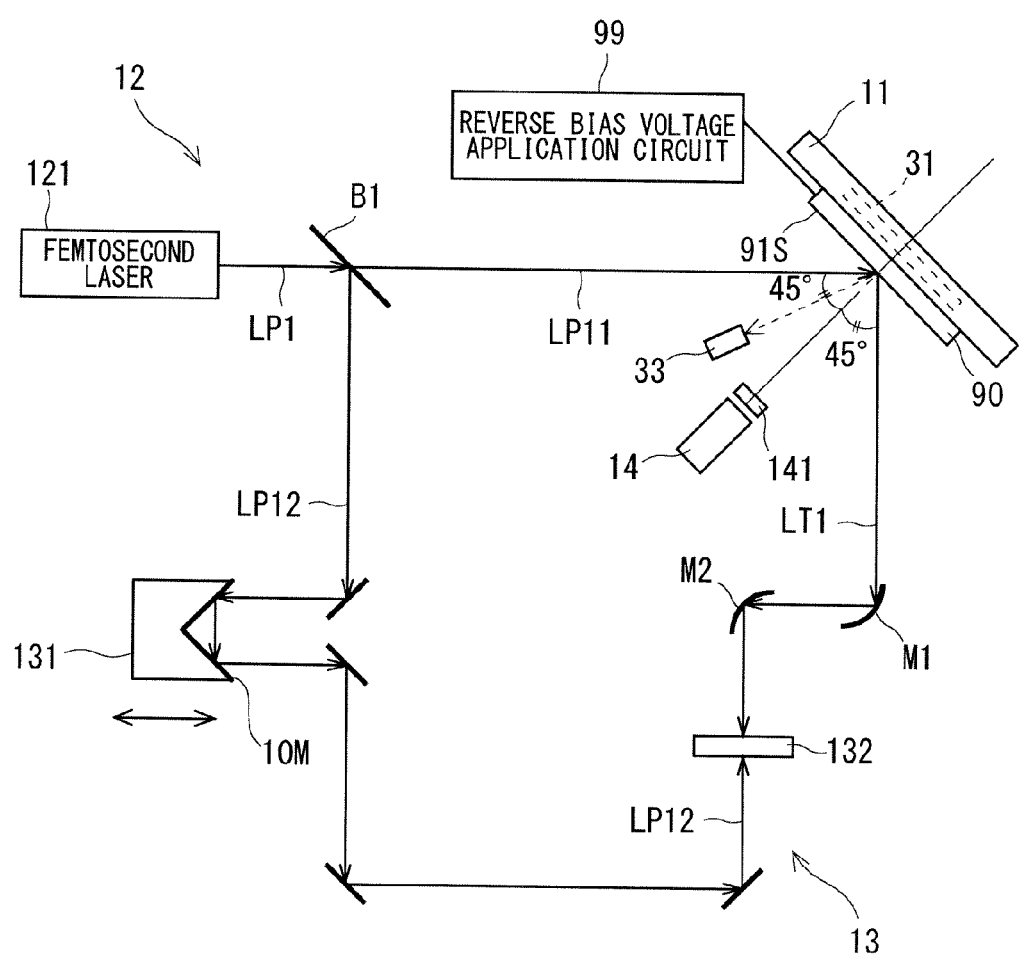

F I G . 4
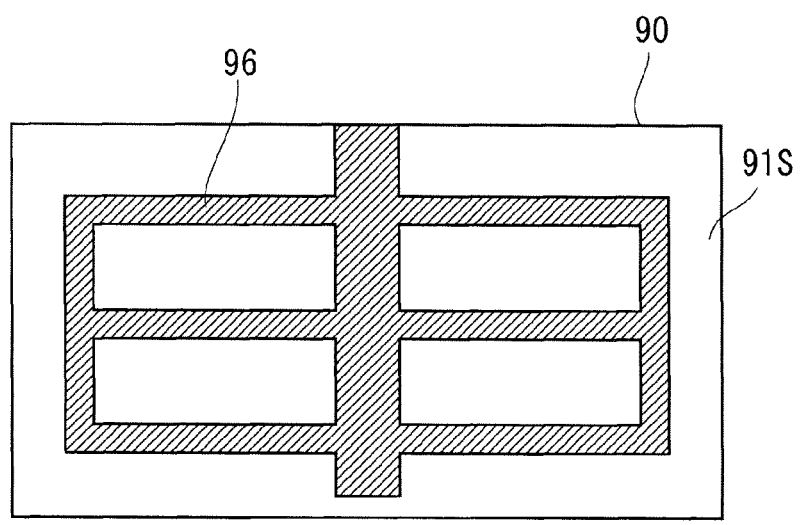

F I G . 5
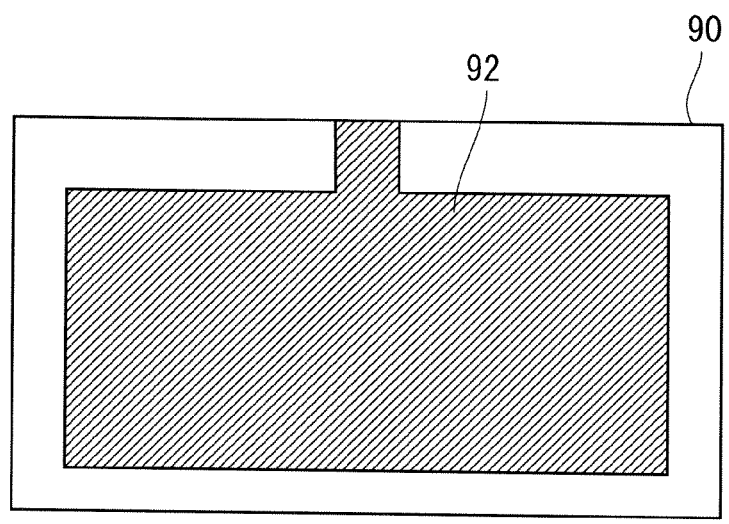

F I G . 8

291

| DEVICE TEMPERATURE | 5 | 10 | 15 | 20 | 25 | 30 | 35 | 40 |
|---|---|---|---|---|---|---|---|---|
| ELECTROMAGNETIC WAVE INTENSITY | 51 | 50.8 | 50.4 | 50 | 49.2 | 48.8 | 48.2 | 47 |
| RELATIVE INTENSITY | 102 | 101.6 | 100.8 | 100 | 98.4 | 97.6 | 96.4 | 94 |

F I G . 9
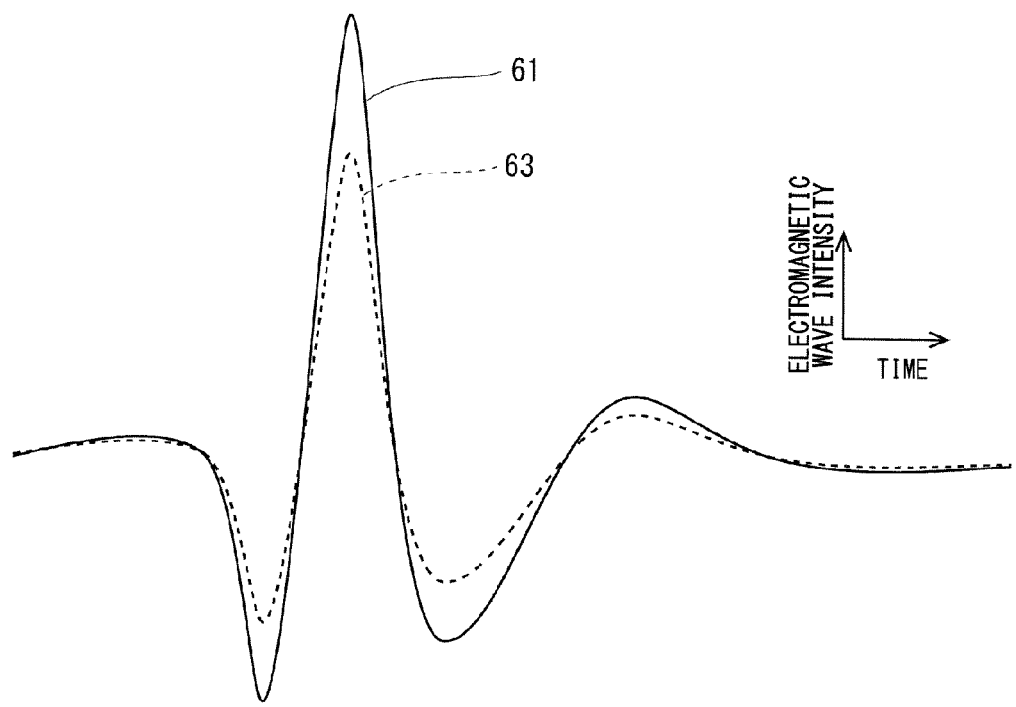

FIG. 10

| ELECTROMAGNETIC WAVE INTENSITY (25°C) | 30 | 45 | 65 | 30 | -10 | -50 | -25 | -3 |
|---|---|---|---|---|---|---|---|---|
| CORRECTED VALUE (20°C) | 30.4878 | 45.73171 | 66.05691 | 30.4878 | -10.1626 | -50.813 | -25.4065 | -3.04878 |

293

F I G . 1 3
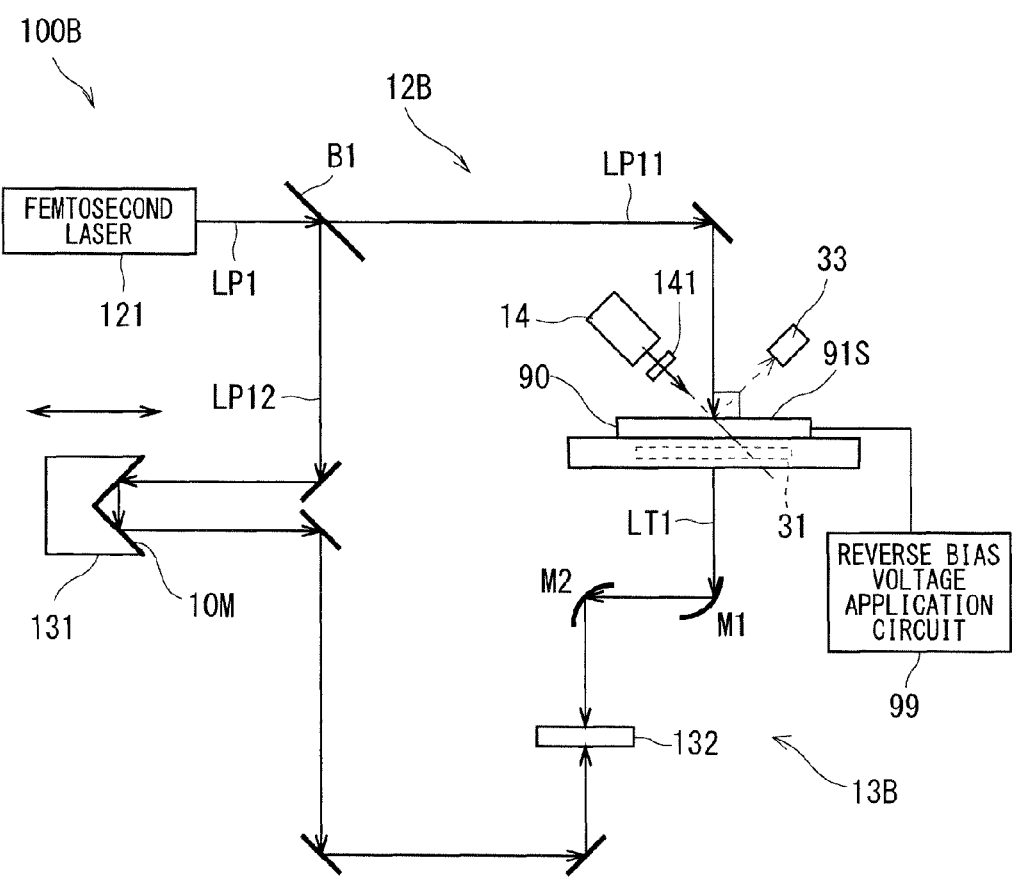

INSPECTION APPARATUS AND INSPECTION METHOD

CROSS-REFERENCE TO RELATED APPLICATIONS

The subject application claims priority to Japanese Patent Application No. 2013-173140 filed Aug. 23, 2013, the subject matter of which is incorporated herein by reference in entirety.

BACKGROUND OF THE INVENTION

1. Field of the Invention

The present invention relates to a technique for inspecting photoelectric devices.

2. Description of the Background Art

As a technique for inspecting photoelectric devices, such a technique is known that inspects a photoelectric device by irradiating the photoelectric device with pulsed light to cause the photoelectric device to radiate an electromagnetic wave, and detecting this electromagnetic wave (for example, Japanese Patent Application Laid-Open No. 2013-019861).

Incidentally, it is general to use semiconductors and metals as materials for producing photoelectric devices. Particularly in semiconductors, when temperature rises, electrons in the valence band thermally jump over the band gap to the conduction band. Distribution of electrons follows the so-called Fermi distribution. Due to thermal influence, electrons and holes move from the donor level and the acceptor level to the conduction band and the valence band, respectively. In other words, there has been a possibility that characteristics of the photoelectric device vary largely depending on temperature. Accordingly, there are needs for techniques to inspect the temperature dependent characteristics of the photoelectric devices.

SUMMARY OF THE INVENTION

The present invention is directed to an inspection apparatus for inspecting a photoelectric device.

An inspection apparatus according to a first aspect includes: an excitation light irradiation part for irradiating the photoelectric device with excitation light to cause the photoelectric device to radiate an electromagnetic wave; a detection part for detecting the electromagnetic wave radiated from the photoelectric device in response to irradiation with the excitation light; and a temperature changing part for changing a temperature of the photoelectric device at a part irradiated with the excitation light.

According to the inspection apparatus of the first aspect, the temperature dependent characteristics of the photoelectric device can be inspected based on the radiated electromagnetic wave.

In addition, a second aspect provides the inspection apparatus of the first aspect, which further includes a temperature measuring part for measuring a temperature of the photoelectric device at the part irradiated with the excitation light.

According to the inspection apparatus of the second aspect, the temperature dependent characteristics of the photoelectric device can be inspected more precisely by measuring the temperature of the photoelectric device.

In addition, a third aspect provides the inspection apparatus of the second aspect, which further includes a storage part for storing temperature correlation information regarding a correlation between the temperature of the photoelectric device and the intensity of the electromagnetic wave radiated from the photoelectric device in response to irradiation with the excitation light; and a correction part for correcting the intensity of the electromagnetic wave detected by the detection part based on the temperature of the photoelectric device obtained by the temperature measuring part and the temperature correlation information.

According to the inspection apparatus of the third aspect, it is possible by the correction to remove a component caused by a temperature fluctuation of the photoelectric device from the detected intensity of the electromagnetic wave. Thus, it is possible to properly inspect the photoelectric device.

In addition, a fourth aspect provides the inspection apparatus of the third aspect, wherein the temperature correlation information is obtained by changing the temperature of the photoelectric device using the temperature changing part, and collecting intensities of the electromagnetic waves radiated from the photoelectric device at respective temperatures.

According to the inspection apparatus of the fourth aspect, the temperature correlation information can be properly obtained.

In addition, a fifth aspect provides the inspection apparatus of any one of the first to fourth aspects, which further includes a continuous light irradiation part for irradiating the photoelectric device with continuous light.

According to the inspection apparatus of the fifth aspect, it is possible to inspect characteristics of the photoelectric device under a condition of generating electricity by the continuous light.

In addition, a sixth aspect provides the inspection apparatus of any one of the first to fifth aspects, which further includes a scanning mechanism for scanning the photoelectric device with the excitation light, an image producing part for producing an electromagnetic wave intensity distribution image showing a distribution of the intensity of the electromagnetic wave radiated from the photoelectric device, and a display part for displaying the electromagnetic wave intensity distribution image.

According to the inspection apparatus of the sixth aspect, it is possible to visually understand the characteristic of each part of the photoelectric device by producing the electromagnetic wave intensity distribution image.

In addition, the present invention is directed to an inspection method for inspecting a photoelectric device.

An inspection method according to a seventh aspect includes the steps of: (a) irradiating the photoelectric device with excitation light; (b) detecting an electromagnetic wave radiated from the photoelectric device in response to irradiation with the excitation light in the step (a); and (c) changing a temperature of the photoelectric device.

Therefore, an object of the present invention is to provide, in a photoelectric device inspection based on electromagnetic wave detection, a technique to inspect temperature dependent characteristics of a photoelectric device.

These and other objects, features, aspects and advantages of the present invention will become more apparent from the following detailed description of the present invention when taken in conjunction with the accompanying drawings.

BRIEF DESCRIPTION OF THE DRAWINGS

FIG. 2 is a schematic configuration diagram showing an irradiation part and a detection part shown in FIG. 1;

FIG. 4 is a plan view of the solar cell panel seen from a light receiving surface side;

FIG. 5 is a plan view of the solar cell panel seen from a back surface side;

FIG. 8 is a diagram showing an example of temperature correlation information;

FIG. 9 is a diagram showing temporal waveforms restored from electromagnetic wave pulses radiated from the solar cell panel;

FIG. 10 is a diagram showing an example of corrected electromagnetic wave intensity;

FIG. 13 is a schematic configuration diagram showing an irradiation part and a detection part included in an inspection apparatus according to a third preferred embodiment.

DESCRIPTION OF THE PREFERRED EMBODIMENTS

Figure 1:
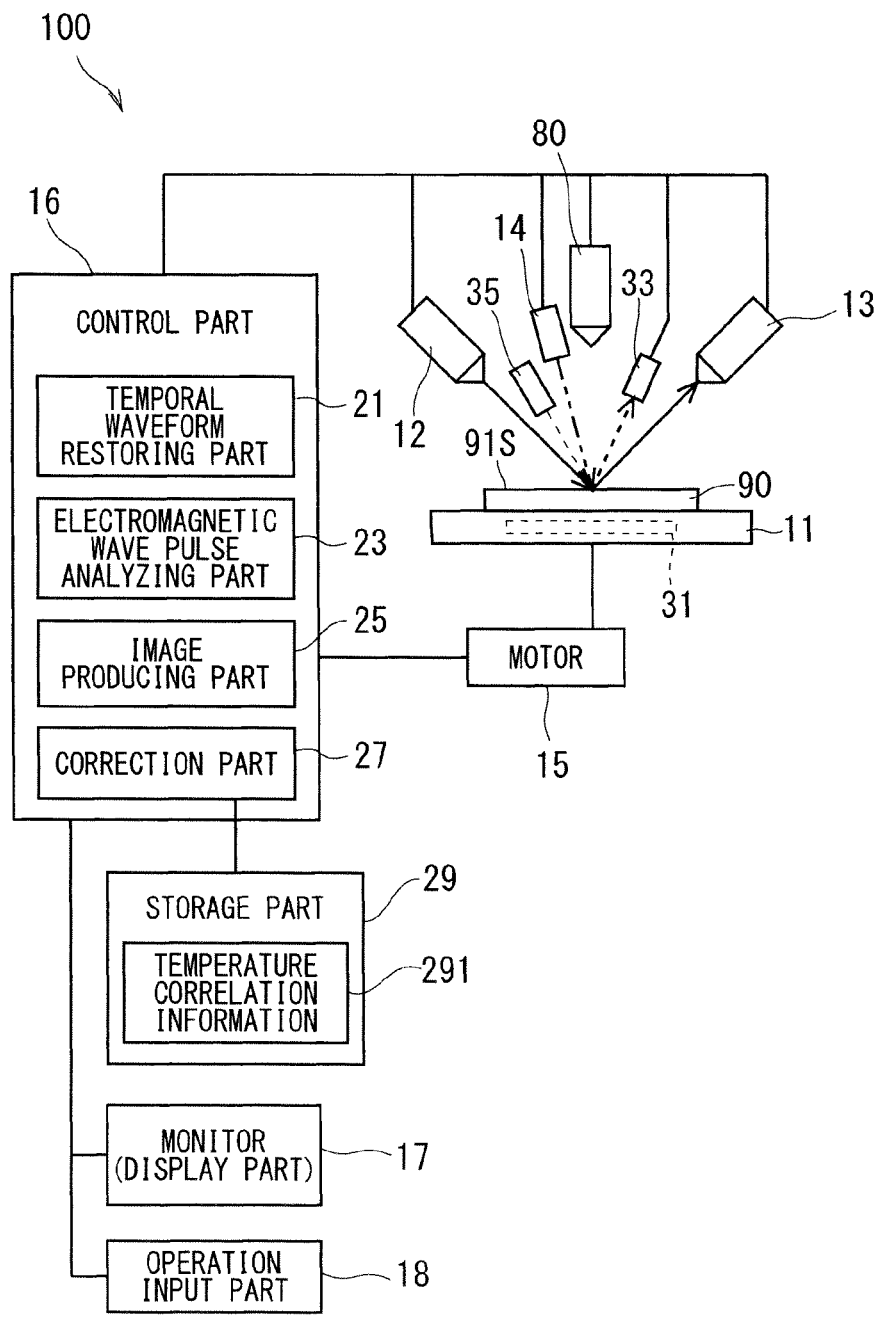
FIG. 1 is a schematic configuration diagram of an inspection apparatus according to a first preferred embodiment.

Hereinafter, preferred embodiments of the present invention will be described with reference to the accompanying drawings. In the drawings, the dimensions of each part or the number of parts may occasionally be exaggerated or simplified as necessary for easy understanding.

<1. First Preferred Embodiment>
<1.1. Configuration and Functions of Inspection Apparatus>

FIG. 1 is a schematic configuration diagram of an inspection apparatus 100 according to a first preferred embodiment. FIG. 2 is a schematic configuration diagram showing an excitation light irradiation part 12 and a detection part 13 shown in FIG. 1.

The inspection apparatus 100 is configured to be suitable to inspect characteristics of a solar cell panel 90, which is a kind of substrate having formed therein a photoelectric device. A photoelectric device such as a photovoltaic cell has, for example, a p-n junction at which a p-type semiconductor and an n-type semiconductor are joined. In the vicinity of the p-n junction, electrons and holes diffuse and combine with each other to cause a diffusion current, so that a depletion layer containing almost no electrons and holes is formed in the vicinity of the p-n junction. In this region, since forces to pull electrons and holes back to the n-type region and the p-type region, respectively, are generated, an electric field (internal electric field) is generated inside the photoelectric device.

Under this condition, if the p-n junction is irradiated with light having energy larger than the band gap, the free electrons and the free holes generated at the p-n junction move by the internal electric field such that the free electrons move to the n-type semiconductor region and the remained free holes move to the p-type semiconductor region. In a photoelectric device, this current is taken out to the outside through electrodes respectively mounted on the n-type semiconductor and the p-type semiconductor. In the case of a photovoltaic cell, for example, movement of electrons and holes caused when the depletion layer at the p-n junction is irradiated with light is used as DC electricity.

The inventors found the fact that irradiation of a photoelectric device with pulsed light having a specified wavelength generates an electromagnetic wave pulse having a particular wavelength. According to the Maxwell's equations, a change in a current generates an electromagnetic wave having intensity proportional to temporal differentiation of the current. That is, irradiation of a photoexcited carrier generating region such as the depletion layer with pulsed light causes instantaneously generation or extinction of a photocurrent. In proportion to temporal differentiation of this instantaneously generated photocurrent, an electromagnetic wave pulse is generated.

Here, the generation of the photocurrent reflects characteristics of the photoexcited carrier generating region such as the depletion layer. Accordingly, characteristics of the photoexcited carrier generating region such as the depletion layer can be inspected by analyzing the generated electromagnetic wave pulse. Based on this principle, the inspection apparatus 100 is configured so as to detect an electromagnetic wave pulse generated when the solar cell panel 90 is irradiated with pulsed light having a specific wavelength.

As shown in FIG. 1, the inspection apparatus 100 includes a stage 11, an excitation light irradiation part 12, a detection part 13, a continuous light irradiation part 14, a motor 15, a control part 16, a monitor (display part) 17, an operation input part 18, a temperature changing part 31, a temperature measuring part 33, a condensation/freezing prevention element 35, and a visible camera 80.

The stage 11 fixes thereon the solar cell panel 90 by fixing element not shown in the figure. The fixing element may be element using a clipping tool that clips the substrate, an adhesive sheet adhered to the substrate, or adsorption holes formed on a surface of the stage 11. However, any other fixing element may be used as long as it can fix the solar cell panel 90. In the present preferred embodiment, the stage 11 holds the solar cell panel 90 such that the excitation light irradiation part 12 can irradiate a light receiving surface 91S side of the solar cell panel 90 with excitation light and that the detection part 13 can detect an electromagnetic wave pulse radiated from the light receiving surface 91S side.

As shown in FIG. 2, the excitation light irradiation part 12 has a femtosecond laser 121. The femtosecond laser 121 radiates pulsed light (pulsed light LP1) having a wavelength in a region including, for example, the visible light region from 360 nm (nanometers) to 1.5 μm (micrometers) (inclusive). As a specific example, linearly polarized pulsed light having a center wavelength around 800 nm, a cycle of several kHz to several hundred MHz, and a pulse width of 10 to 150 femtosecond is radiated from the femtosecond laser. Needless to say, the femtosecond laser may be designed to radiate pulsed light in other wavelength region (for example, a visible light wavelength such as a blue wavelength (450 to 495 nm) or a green wavelength (495 to 570 nm)).

The pulsed light LP1 outputted from the femtosecond laser 121 is split to two by a beam splitter B1. One of the split pulsed light (pulsed light LP11) is applied to the solar cell panel 90. At this time, the excitation light irradiation part 12 irradiates the light receiving surface 91S side with the pulsed light LP11. In addition, the pulsed light LP11 is applied to the solar cell panel 90 such that the light axis of the pulsed Light LP11 is oblique with respect to the light receiving surface 91S of the solar cell panel 90. In the present preferred embodiment, the irradiation angle is set such that the incident angle becomes 45 degrees. However, the incident angle is not limited to this angle, but may be appropriately changed within the range of 0 to 90 degrees.

Figure 3:
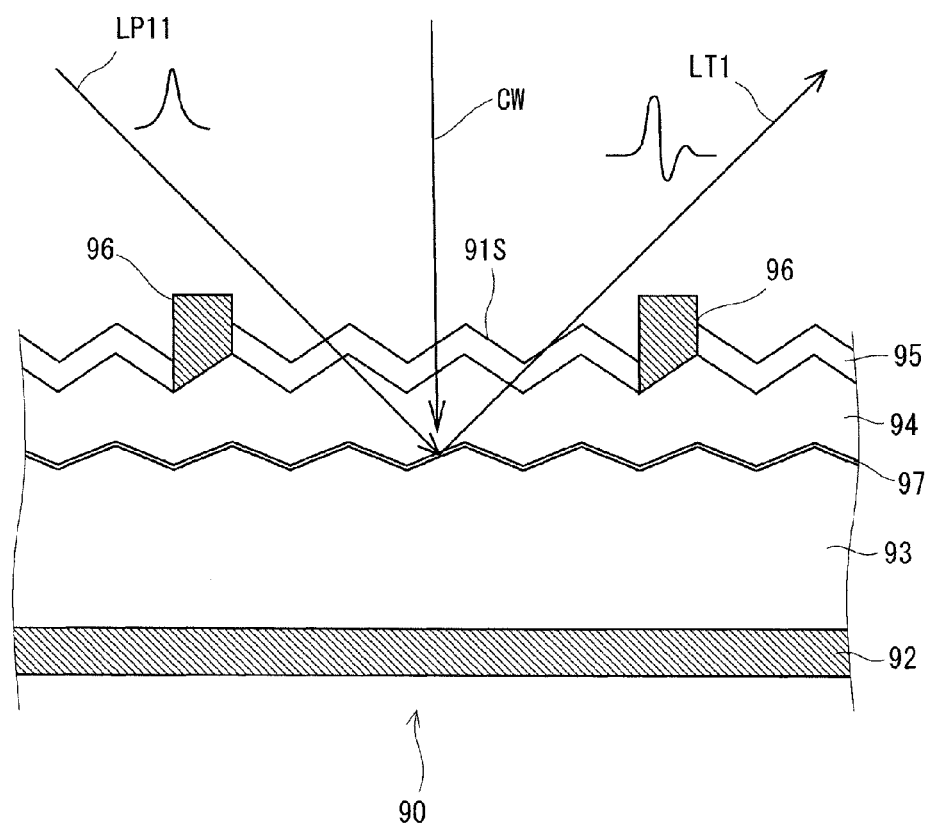
FIG. 3 is a schematic sectional view of a solar cell panel.

FIG. 3 is a schematic sectional view of the solar cell panel 90. FIG. 4 is a plan view of the solar cell panel 90 seen from the light receiving surface 91S side. FIG. 5 is a plan view of the solar cell panel 90 seen from its back surface side. The solar cell panel 90 is configured as a crystalline silicon solar cell panel. The solar cell panel 90 is configured as a crystalline silicon photovoltaic cell having a laminated structure composed of, in order from the bottom, a back surface electrode 92 formed of aluminum or the like in a flat plate shape, a p-type silicon layer 93, an n-type silicon layer 94, a antireflection film 95, and a lattice-shaped light receiving surface electrode 96. The antireflection film 95 is formed of silicon oxide, silicon nitride or titanium oxide.

Of the main surfaces of the solar cell panel 90, the main surface on which the light receiving surface electrode 96 is formed becomes the light receiving surface 91S. In other words, the solar cell panel 90 is designed to generate electricity by receiving light from the light receiving surface 91S side. The light receiving surface electrode 96 may be made of a transparent electrode. Incidentally, the inspection apparatus 100 may be used to inspect photovoltaic cells other than the crystalline silicon type photovoltaic cell (such as the amorphous silicon type photovoltaic cell). The amorphous silicon photovoltaic cell generally has an energy gap in the range of 1.75 eV to 1.8 eV, which is larger than the energy gap 1.2 eV of the crystalline photovoltaic cell. In this case, it is possible to cause the amorphous silicon photovoltaic cell to successfully generate a terahertz wave by making the wavelength of the femtosecond laser 121 to be, for example, 700 μM or shorter. The same thought can be applied to the other semiconductor photovoltaic cells (such as the CIGS type or the GaAs type).

The light receiving surface 91S of the solar cell panel 90 has a necessary textured structure to suppress reflection loss of light. Specifically, the textured structure is a pattern of several μm to several tens of μm concavo-convex formed by anisotropic etching or the like or V-shaped grooves formed by a mechanical method. In this manner, the light receiving surface 91S of the solar cell panel 90 is generally formed so as to let in light as efficiently as possible. Accordingly, pulsed light having a specific wavelength applied to the light receiving surface is allowed to easily reach the p-n junction part 97. In the case of a solar cell panel, for example, light having a wavelength of 1 μM or shorter including mainly the visible light wavelength region can easily reach the p-n junction part 97. As described above, if the solar cell panel 90 is placed on the inspection apparatus 100 such that the main surface receiving light in the actually used condition becomes the light receiving surface, the electromagnetic wave pulse LT1 can be successfully generated.

In addition, the junction of the p-type silicon layer 93 and the n-type silicon layer 94 is the p-n junction part 97, in which the depletion layer is formed. By irradiating this portion with the pulsed light LP11, an electromagnetic wave pulse is generated and radiated out. In the present preferred embodiment, the electromagnetic wave pulse detected by the detection part 13 is an electromagnetic wave pulse (hereinafter referred to as an electromagnetic wave pulse LT1) mainly in the terahertz region (frequency range of 0.01 THz to 10 THz).

Incidentally, the substrate to be inspected by the inspection apparatus 100 is not limited to the solar cell panel 90. Any substrate containing a photoelectric device that converts light containing visible light components to an electric current may be an object to be inspected by the inspection apparatus 100. The photoelectric device other than the solar cell panel 90 may specifically be an image sensor such as a CMOS sensor and a CCD sensor. As an image sensor, such a sensor is known that has a substrate containing a photoelectric device with a light receiving element formed on a surface which becomes a back surface side of the substrate under an actually used condition. Even in the case of such a substrate, the electromagnetic wave pulse LT1 can properly be detected if the substrate is placed on the inspection apparatus 100 such that the main surface receiving light in the actually used condition becomes the light receiving surface.

Referring back to FIG. 2, the other pulsed light split by the beam splitter B1 passes through a delay part 131 and mirrors, and enters a detector 132 as probe light LP 12. On the other hand, the electromagnetic wave pulse LT1 generated in response to the irradiation with the pulsed light LP11 is converged by parabolic mirrors M1 and M2 to enter the detector 132.

The detector 132 has, for example, a photoconductive switch as an electromagnetic wave detection element. When the probe light LP12 is applied to the detector 132 under the condition that the electromagnetic wave pulse enters the detector 132, a current responsive to the electric field strength of the electromagnetic wave pulse LT1 is generated instantaneously in the photoconductive switch. This current responsive to the electric field strength is converted to a digital quantity through an I/V conversion circuit and an A/D conversion circuit. In this manner, the detection part 13 detects the electric Field strength of the electromagnetic wave pulse LT1 transmitted through the solar cell panel 90 in response to irradiation with the probe light LP12. Other elements, for example, nonlinear optical crystals may be used for the detector 132.

The delay part 131 is an optical element for continuously changing the time required for the probe light LP12 to reach the detector 132 from the beam splitter B1. The delay part 131 is configured so as to be linearly movable along the incident direction of the probe light LP12 by a moving stage not shown in the figure. In addition, the delay part 131 has a double-reflection mirror 10M for turning the probe light LP12 back to the incident direction.

The delay part 131 moves the double-reflection mirror 10M by driving the moving stage based on control by the control part 16 to precisely change the optical path length of the probe light LP12. In this manner, the delay part 131 changes a time difference between a time the electromagnetic wave pulse LT1 reaches the detection part 13 and a time the probe light LP12 reaches the detection part 13. Accordingly, by changing the optical path length of the probe light LP12 by the delay part 131, it is possible to delay a timing (detection timing or sampling timing) at which the detection part 13 (the detector 132) detects the electric field strength of the electromagnetic wave pulse LT1.

The time the probe light LP12 reaches the detector 132 may be changed in another manner. Specifically, an electro-optic effect may be used. That is, an electro-optic element which changes refractive index in response to a change in an applied voltage may be used as a delay element. Specifically, an electro-optic element as disclosed in Japanese Patent Application Laid-Open No. 2009-175127 can be used.

Alternatively, the optical path length of the pulsed light LP11 (pump light) or the optical path length of the electromagnetic wave pulse LT1 radiated from the solar cell panel 90 may be changed. In this case also, it is possible to shift the time the electromagnetic wave pulse LT1 reaches the detector 132 relative to the time the probe light LP12 reaches the detector 132. In this manner, it is possible to delay the timing to detect the electric field strength of the electromagnetic wave pulse LT1 at the detector 132.

Further, the solar cell panel 90 is connected with a reverse bias voltage application circuit 99 which applies a reverse bias voltage between the back surface electrode 92 and the light receiving surface electrode 96 during the inspection. Application of the reverse bias voltage between the electrodes increases the width of the depletion layer at the p-n junction part 97, so that the internal electric field can be increased. Since the electric field strength of the electromagnetic wave pulse LT1 detected by the detector 132 can be increased, the sensitivity of detecting the electromagnetic wave pulse LT1 by the detector 132 can be improved. However, the reverse bias voltage application circuit 99 may be omitted.

The continuous light irradiation part 14 irradiates the solar cell panel 90 with continuous light CW. The kind of the continuous light CW outputted from the continuous light irradiation part 14 is appropriately selected according to the purpose of inspection, and thus may not be limited. Specifically, however, the continuous light CW may be light containing a plurality of wavelengths such as the sunlight or a pseudo sunlight imitating the sunlight, light from an incandescent lamp, which has a relatively wide range of wavelength distribution, or light from a LED lamp or a fluorescent lamp, which has wavelengths mainly corresponding to the three primary colors of R, G, and B (for example, 400 nm, 600 nm, and 800 nm). The continuous light CW may also be single wavelength light selected within the range from ultraviolet to near-infrared.

The continuous light irradiation part 14 is configured according to the wavelength of the light used for inspection. Specifically, the continuous light irradiation part 14 is configured by a semiconductor laser, a LED, a halogen lamp, or a xenon lamp or a combination of these. In addition, a wavelength variable laser may be used as the continuous light irradiation part 14. A laser used as the wavelength variable laser may be a distributed feedback (DFB) laser, which can change the wavelength of its output laser beam almost continuously (for example, in steps of 2 nm) by, for example, temperature control.

By irradiation of the continuous light CW to the position irradiated with the pulsed light LP11, the inspection apparatus 100 can generate the electromagnetic wave pulse LT1 under the condition being irradiated with the continuous light CW (i.e., the condition that an electromotive force is generated). For example, by irradiating the solar cell panel 90 with the pseudo sunlight, it is possible to simulate a condition being exposed to the sunlight outdoor or the like. By analyzing the electromagnetic wave pulse LT1 generated under this condition, it is possible to detect a structural defect, which would possibly become a problem during the use of the solar cell panel 90, or to evaluate the performances of the solar cell panel 90. Further, by irradiation of the continuous light CW limited to have a particular wavelength, it is possible to inspect wavelength-dependent characteristics of the solar cell panel 90.

The continuous light irradiation part 14 has an irradiation condition changing part 141 (see FIG. 2). The irradiation condition changing part 141 changes the spot diameter of the continuous light CW simultaneously applied to the solar cell panel 90. By changing the area simultaneously irradiated with the continuous light CW by the irradiation condition changing part 141, the area of the region in which an electromotive force is generated can be arbitrarily changed.

In a case that the beam diameter (irradiation diameter) of the pulsed light LP11 is 50 μm, for example, if the beam diameter (irradiation diameter) of the continuous light CW is made to be 50 μm or larger, the part surrounding the region irradiated with the pulsed light LP11 can also be made in the condition that an electromotive force is generated. In this case, it is highly possible that the photoexcited carriers generated by the irradiation of the pulsed light LP11 are affected by the surrounding part. Accordingly, for the solar cell panel 90 to be inspected in the using condition, it is preferable to irradiate also the surrounding part with the continuous light CW. Further, the continuous light CW may not necessarily be locally applied in the spot form, but may be applied to, for example, the entire solar cell panel 90 simultaneously.

The irradiation condition changing part 141 changes also the light intensity of the continuous light CW. By changing the light intensity of the continuous light CW applied to the solar cell panel 90, it is possible to arbitrarily change the magnitude of the generated electromotive force. In this manner, inspection according to the power generating state of the solar cell panel 90 can be realized. Element for changing the light intensity of the continuous light CW may, for example, be the use of a light-blocking filter, but not be limited thereto. Needless to say, the light intensity of the continuous light CW outputted from the continuous light irradiation part 14 may directly be changed.

A motor 15 shown in FIG. 1 drives an X-Y table, not shown in the figure, to move the stage 11 in a two-dimensional plane. The motor 15 drives the X-Y table so as to move the solar cell panel 90 held on the stage 11 relative to the excitation light irradiation part 12. The inspection apparatus 100 can move the solar cell panel 90 by the motor 15 to an arbitrary position in the two-dimensional plane. By using the motor 15, the inspection apparatus 100 can apply the pulsed light LP11 to and inspect a wide area (an inspection target area) of the solar cell panel 90. The motor 15 may be omitted, and the stage 11 may be manually moved by an operator.

Instead of moving the solar cell panel 90 or together with moving the solar cell panel 90, such moving element may be provided that moves the excitation light irradiation part 12 and the detection part 13 in a two-dimensional plane. In this case also, the electromagnetic wave pulse LT1 can be detected in each area of the solar cell panel 90. In addition, the optical path of the pulsed light LP11 may be changed by a galvano mirror or the like so as to scan the solar cell panel 90 with the pulsed light LP11.

The control part 16 is configured as a general computer provided with a CPU, a ROM, a RAM and auxiliary storage part (for example, a hard disk), which are not shown in the figure. The control part 16 is connected to the femtosecond laser 121 of the excitation light irradiation part 12, the delay part 131 and the detector 132 of the detection part 13, the irradiation condition changing part 141 of the continuous light irradiation part 14, and the motor 15 to control operation of these components and receive data from these components.

The control part 16 is further provided with a temporal waveform restoring part 21, an electromagnetic wave pulse analyzing part 23, an image producing part 25, and a correction part 27. These processing parts can be realized by operation of the CPU based on programs not shown in the figure. However, a part or whole of the functions of these parts may be realized in hardware by dedicated operation circuits.

The temporal waveform restoring part 21 constructs a temporal waveform (time waveform) of the electromagnetic wave pulse LT1 generated by the solar cell panel 90 based on the electric field strength detected by the detection part 13 (the detector 132). Specifically, the optical path length of the probe light LP12 (a first optical path length) is changed by moving the double-reflection mirror 10M of the delay part 131 to change the time the probe light reaches the detector 132. As a result, the timing at which the electric field strength of the electromagnetic wave pulse LT1 in the detector 132 is detected is changed. Accordingly, the temporal waveform restoring part 21 detects the electric field strength of the electromagnetic wave pulse LT1 in different phases and plots the detection results on a temporal axis to restore a temporal waveform of the electromagnetic wave pulse LT1.

The electromagnetic wave pulse analyzing part 23 analyzes the temporal waveform restored by the temporal waveform restoring part 21. With respect to the temporal waveform of the electromagnetic wave pulse LT1 having been restored by the temporal waveform restoring part 21, the electromagnetic wave pulse analyzing part 23 performs peak detection of the electric field strength or frequency analysis by the Fourier transform. In this manner, characteristics of the solar cell panel 90 can be analyzed.

The image producing part 25 produces, with respect to the inspection target area of the solar cell panel 90 (a part or whole of the solar cell panel 90), a visualized distribution image (an electromagnetic wave intensity distribution image) of the electric field strength of the electromagnetic wave pulse LT1 radiated in response to the irradiation with the pulsed light LP11. The electromagnetic wave intensity distribution image is such an image that each position irradiated with the pulsed light LP11 is colored or patterned according to the electric field strength of the detected electromagnetic wave pulse LT1.

The correction part 27 corrects the intensity of the electromagnetic wave pulse LT1 detected by the detector 132 of the detection part 13 based on the temperature of the solar cell panel 90 and temperature correlation information 291 which will be described later. The temperature of the solar cell panel 90 is obtained by a temperature measuring part 33 which will be described later. The temperature correlation information 291, which is stored in a storage part 29 connected to the control part 16, is information regarding a correlation between the temperature of the solar cell panel 90 and the intensity of the electromagnetic wave pulse LT1 radiated from the solar cell panel 90 in response to irradiation with the pulsed light LP11 at the temperature. Details of the temperature correlation information 291 will be described later.

The control part 16 is connected to the monitor 17 and the operation input part 18. The monitor 17 is a display device such as a liquid crystal display, and displays various kinds of image information for the operator. The images displayed on the monitor 17 include an image of the light receiving surface 91S of the solar cell panel 90 taken by a visible camera 80, the temporal waveform of the electromagnetic wave pulse LT1 restored by the temporal waveform restoring part 21, and an analyzed result by the electromagnetic wave pulse analyzing part 23. The monitor 17 also displays the electromagnetic wave intensity distribution image produced by the image producing part 25. Further, the monitor 17 appropriately displays a GUI (Graphical User Interface) screen necessary for the operator to set inspection conditions and the like.

The operation input part 18 is configured by various input devices such as a mouse and a keyboard. The operator can perform various operation inputs with respect to the inspection apparatus 100 through the operation input part 18. In addition, the monitor 17 may be configured as a touch panel to function as the operation input part 18.

The temperature changing part 31 warms or cools the solar cell panel 90 at the part irradiated with pulsed light LT11. The temperature changing part 31 can be configured by, for example, a Peltier element or the like embedded in the stage 11. The temperature changing part 31 may be disposed so as to either locally warm or cool only the part irradiated with the pulsed light LT11 or entirely warm or cool the solar cell panel 90. In the present preferred embodiment, the temperature changing part 31 is configured to be able to change the device temperature of the solar cell panel 90 in the range from—20° C. to +80° C.

The temperature measuring part 33 measures the temperature of the solar cell panel 90 at the part irradiated with the pulsed light LT11. The temperature measuring part 33 is preferably configured by a radiation thermometer, which measures a temperature of an object by measuring the intensity of an infrared ray or a visible light ray radiated from the object. Since non-contact measurement of temperature of the solar cell panel 90 is possible by the radiation thermometer, contamination of the solar cell panel 90 can be suppressed, and the temperature can be measured in a short time. In the case of using the radiation thermometer, precise temperature measurement is possible by setting a characteristic emissivity of the solar cell panel 90. Needless to say, a contact-type thermometer or the like may be used in place of the radiation thermometer.

The condensation/freezing prevention element 35 prevents condensation on or freezing of the solar cell panel 90 when the solar cell panel 90 is cooled. The condensation/freezing prevention element 35 may, for example, be such element that supplies a dry gas ($N_2$, Ar, He, Kr or Xe gas or a mixture of these gases) in an air curtain-like manner to the temperature-changed part of the solar cell panel 90. Alternatively, the condensation/freezing prevention element 35 may be such element that prevents condensation on or freezing of the solar cell panel 90 by decompressing the area surrounding the solar cell panel 90.

<1.2. Inspection of Solar Cell Panel>

Next, exemplary inspections of the solar cell panel 90 that can be performed by the inspection apparatus 100 will be described. It should be understood, in the following description, that each operation of the inspection apparatus 100 is carried out under control of the control part 16 unless otherwise specified. It should also be understood that, depending on the contents of each step, a plurality of steps may be carried out in parallel or the order of carrying out a plurality of steps may be appropriately changed.

<1.2.1 Inspection Example 1>

Figure 6:
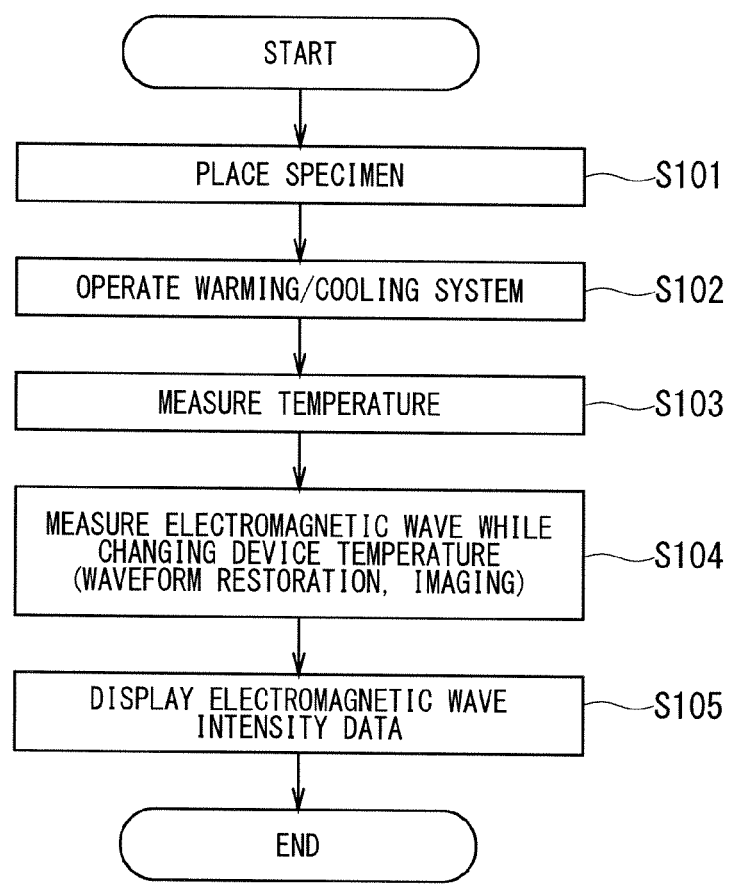
FIG. 6 is a flowchart of Example 1 of inspecting a solar cell panel.

FIG. 6 is a flowchart of Example 1 of inspecting the solar cell panel 90. In Inspection Example 1, temperature dependent characteristics of the solar cell panel 90 which is a photoelectric device are inspected.

In Inspection Example 1, the solar cell panel 90 as a specimen is placed on the stage 11 (step S101 in FIG. 6). At this time, as described above, the solar cell panel 90 is placed such that the pulsed light LP11 is applied to the light receiving surface 91S (that is, the main surface at the side receiving sunlight in the condition that the solar cell panel 90 is actually used).

When the solar cell panel 90 is placed on the stage 11, the reverse bias voltage application circuit 99 is connected to the back surface electrode 92 and the light receiving surface electrode 96 of the solar cell panel 90, and applies a reverse bias voltage to the back surface electrode 92 and the light receiving surface electrode 96. In the case where the reverse bias voltage needs not be applied, however, this step can be omitted.

When the solar cell panel 90 is placed, the warming/cooling system is operated (step S102 in FIG. 6). In detail, the temperature changing part 31 is operated. This allows the temperature of the solar cell panel 90 to be changed. Then, the temperature of the solar cell panel 90 is measured (step S103 in FIG. 6). In detail, the temperature of the solar cell panel 90 is measured by the temperature measuring part 33.

Electromagnetic wave measurement while changing the device temperature of the solar cell panel 90 is performed (step S104 in FIG. 6). In detail, the pulsed light LP11 is applied to the solar cell panel 90 warmed or cooled to be each temperature in the range of, for example, −20° C. to +80° C., and the electromagnetic wave measurement is carried out. When the temperature of the solar cell panel 90 is changed, the condensation/freezing prevention element 35 is appropriately driven.

In step S104, at least one of the electromagnetic wave measurement for restoring the temporal waveform of the electromagnetic wave pulse LT1 and the electromagnetic wave measurement for imaging is carried out.

<Temporal Waveform Restoration>

In the electromagnetic wave measuring for the temporal waveform restoration, the timing of detecting the electromagnetic wave pulse LT1 at the detector 132 is changed by adjusting the delay part 131. The intensity of the electromagnetic wave pulse LT1 is measured at the plurality of changed detection timings. By detecting the intensity of the radiated electromagnetic wave pulse LT1 while changing the detection timing in this manner, the intensity of the electromagnetic wave pulse LT1 can be measured in each phase. Accordingly, the temporal waveform of the electromagnetic wave pulse LT1 can be restored. The position at which the electromagnetic wave pulse LT1 is measured may be a single point or a plurality of points on the solar cell panel 90.

The temporal waveform restoring part 21 restores the temporal waveform of the electromagnetic wave pulse LT1. When the temporal waveform has been restored, analysis of the electromagnetic wave pulse LT1 is carried out by the electromagnetic wave pulse analyzing part 23 as needed.

<Imaging>

In the electromagnetic wave measurement for imaging, a specific inspection target area of the solar cell panel 90 is scanned with the pulsed light LT11, and the electromagnetic wave intensity of the electromagnetic wave pulse LT1 radiated from each point in the inspection target area is detected. Further, the image producing part 25 produces an electromagnetic wave intensity distribution image based on data regarding the detected electromagnetic wave intensity. In this manner, imaging to visualize the electromagnetic wave intensity distribution as an image is performed.

When the electromagnetic wave measurement has been completed, the electromagnetic wave intensity data are displayed on the monitor 17 (step S105 in FIG. 6). In detail, the data displayed on the monitor 17 include the temporal waveform restored from the electromagnetic wave intensity detected in step S104, analyzed result of the electromagnetic wave pulse, or the image (the electromagnetic wave intensity distribution image) produced by the imaging processing in step S104.

For example, in step S105, the image producing part 25 may produce a differential image between two electromagnetic wave intensity distribution images obtained at different device temperatures from each other, and display the differential image on the monitor 17. According to this differential image, it is possible to easily identify an area in which the temperature dependent characteristic is remarkable in the solar cell panel 90.

According to Inspection Example 1, as described above, detection of the electromagnetic wave pulse LT1 is performed while changing the solar cell panel 90 from a low temperature state to a high temperature state. Therefore, the temperature dependent characteristics of the solar cell panel 90 can be inspected.

<1.2.2. Inspection Example 2>

Figure 7:
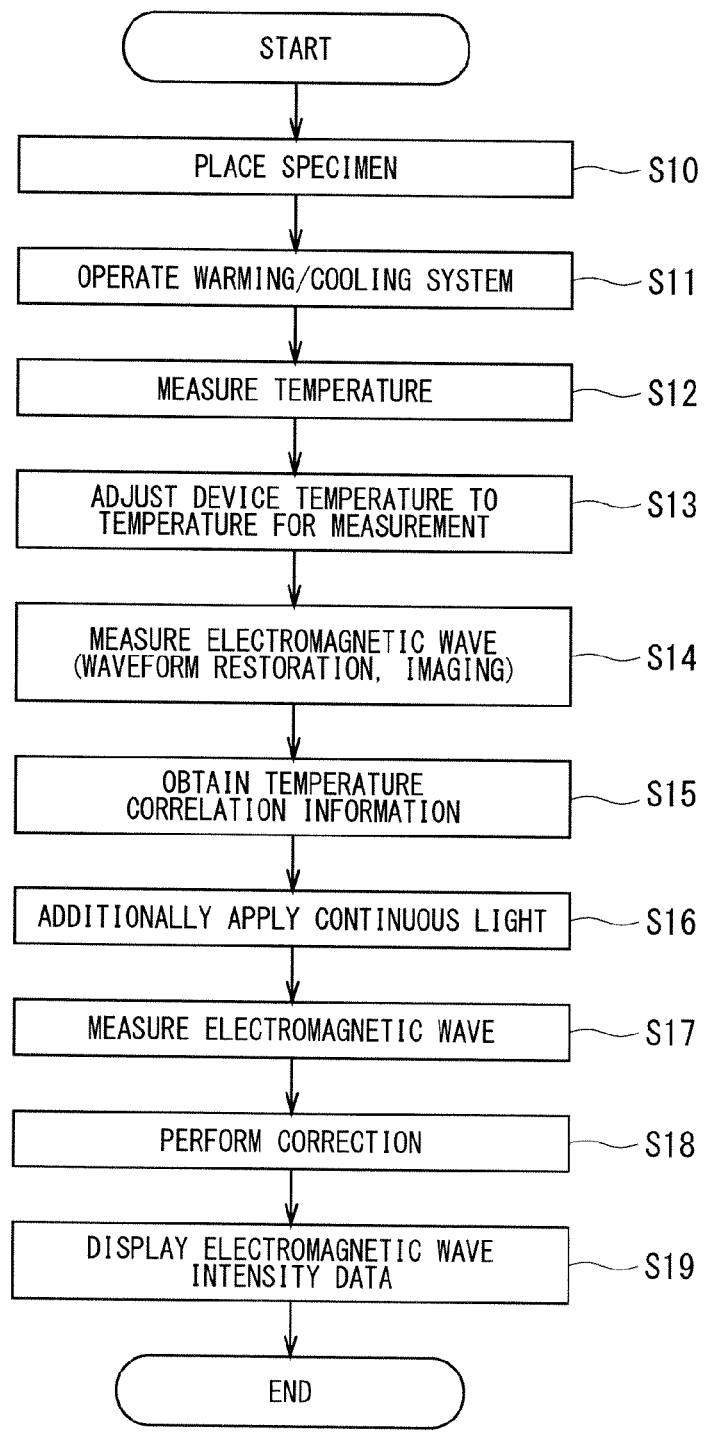
FIG. 7 is a flowchart of Example 2 of inspecting a solar cell panel.

FIG. 7 is a flowchart of Example 2 of inspecting the solar cell panel 90. In this Inspection Example 2, influence of the change in the device temperature on the electromagnetic wave intensity is considered to inspect the solar cell panel 90 with high accuracy.

In detail, first, the solar cell panel 90 as a specimen is placed on the stage 11 (step S10 in FIG. 7). Then, the warming/cooling system is operated (step S11 in FIG. 7). Further, the temperature of the solar cell panel 90 is measured (step S12 in FIG. 7).

After the operation of the warming/cooling system and the measurement of the device temperature are completed, the device temperature of the solar cell panel 90 is adjusted to be a temperature for measurement (for example, a room temperature) (step S13 in FIG. 7). As a result, the temperature of the solar cell panel 90 is changed to be and maintained at the temperature for measurement.

Device temperature fluctuation may possibly cause fluctuation in the quantity of the thermally-excited carriers. Therefore, the temperature-dependent fluctuation components of the carriers can be removed by keeping the device temperature constant. As a result, in the electromagnetic wave pulse LT1 radiated from the solar cell panel 90, the components dependent on the irradiation with the pulsed light LP11 can be measured more accurately.

After the device temperature adjustment is completed, an electromagnetic wave measurement is performed (step S14 in FIG. 7). In also step S14, at least one of an electromagnetic wave measurement for restoring the temporal waveform of the electromagnetic wave pulse LT1 and an electromagnetic wave measurement for imaging is carried out.

After an electromagnetic wave measurement according to a desired inspection requirement is performed in step S14, the temperature correlation information 291 is obtained (step S15 in FIG. 7). In step S15, the temperature correlation information 291 can be obtained by changing the temperature of the solar cell panel 90 by the temperature changing part 31 and collecting the electromagnetic wave intensities of the electromagnetic wave pulse LT1 radiated from the solar cell panel 90 at respective temperatures. The process in step S15 may be performed before steps S13 and S14.

FIG. 8 is a diagram showing an example of the temperature correlation information 291. A shown in FIG. 8, the temperature correlation information 291 includes the intensity of the electromagnetic wave radiated at each of the temperatures of the solar cell panel 90 changed from 5° C. to 40° C. in steps of 5° C. The temperature correlation information 291 further includes a relative intensity which is a relative value of the electromagnetic wave intensity at each temperature to a value of the electromagnetic wave intensity at the device temperature of 20° C. set as a reference value of "100".

The temperature correlation information 291 can be obtained by determining one position on the solar cell panel 90 as a representative point, and detecting the electromagnetic wave pulse LT1 radiated when the representative point is irradiated with the pulsed light LP11, which is the excitation light. Needless to say, it is also possible to use measurement results obtained at the plurality of positions. In addition, the temperature correlation information 291 is obtained by detecting the electromagnetic wave pulse LT1 at a particular detection timing under a condition that the delay part 131 is fixed. Alternatively, the temperature correlation information may be obtained by measuring the electromagnetic wave intensity at the plurality of positions, and averaging a plurality of electromagnetic wave intensities measured at a same temperature. In this case, the measurement error of the electromagnetic wave intensity can be decreased.

In the photoelectric device, carriers are excited by heat with the rise of the temperature. These carriers, which are called the dark current, reduce the internal electric field of the photoelectric device. Accordingly, as shown by the temperature correlation information 291, the electromagnetic wave intensity decreases with the rise of the device temperature.

Referring back to FIG. 7, after the temperature correlation information 291 has been obtained, the continuous light irradiation part 14 irradiates the solar cell panel 90 with the continuous light CW (step S16 in FIG. 7). Accordingly, the part irradiated with the pulsed light LP11 is additionally irradiated with the continuous light CW.

Under irradiation with the continuous light CW, an electromagnetic wave measurement is performed (step S17 in FIG. 7). The electromagnetic wave measurement in step S17 is almost the same as the electromagnetic wave measurement in step S14 except that the continuous light CW is applied. That is, the electromagnetic wave measurement for restoring the temporal waveform or the electromagnetic wave measurement for imaging, which has been carried out in step S14, is carried out again under irradiation with the continuous light CW. Here, the conditions for irradiation with the continuous light CW may be appropriately set depending on the purpose of inspection. According to the set conditions, the irradiation condition changing part 141 changes the conditions for irradiation with the continuous light CW.

FIG. 9 is a diagram showing temporal waveforms 61 and 63 restored from the electromagnetic wave pulses LT1 radiated from the solar cell panel 90. In FIG. 9, the horizontal axis shows time, and the vertical axis shows electromagnetic wave intensity. The temporal waveform 61 corresponds to the electromagnetic wave pulse LT1 radiated from the solar cell panel 90 in response to the irradiation with the pulsed light LP11 without irradiation with the continuous light CW. On the other hand, the temporal waveform 63 corresponds to the electromagnetic wave pulse LT1 radiated in response to the irradiation with the pulsed light LP11 under the condition of irradiation with the continuous light CW.

As shown in FIG. 9, it is found, from comparison of the two temporal waveforms 61 and 63, that the amplitude of the electromagnetic wave pulse LT1 is relatively reduced by the irradiation of the continuous light CW. The reason for this can be thought as described below. That is, by the irradiation of the continuous light CW, the photoexcited carriers are excited, and cause a state to fill the conduction band. In this state, change in the current of the photoexcited carriers generated by the pulsed light LP11 is relatively reduced. As a result, the electric field strength of the generated electromagnetic wave pulse LT1 is thought to be also reduced. However, depending on the conditions for the irradiation of the continuous light CW, it may possibly happen that the amplitude of the electromagnetic wave pulse LT1 relatively increases.

Referring back to FIG. 7, after the electromagnetic wave measurement in step S17 is completed, a process of correcting the electromagnetic wave intensity is performed by the correction part 27 (step S18 in FIG. 7). The correction part 27 corrects the electromagnetic wave intensity obtained in step S17 based on the temperature correlation information 291 obtained in step S15.

The present preferred embodiment is configured such that the device temperature is maintained at a specified temperature (20° C. here) by the temperature changing part 31. Therefore, the device temperature hardly fluctuates. However, there is a possibility that fluctuations in the device temperature would occur due to changes in environmental temperature, the irradiation of the continuous light CW or excitation light or the like. Accordingly, the correction process is performed to remove variations in the electromagnetic wave intensity dependent on fluctuations in the device temperature.

FIG. 10 is a diagram showing an example of corrected electromagnetic wave intensity 293. The values of the corrected electromagnetic wave intensity 293 shown in FIG. 10 are those obtained by correcting the values of the electromagnetic wave intensity measured at the device temperature of 25° C. to values of the electromagnetic wave intensity supposed to be observed at 20° C. According to the temperature correlation information 291, it is found that the electromagnetic wave intensity in the case at the device temperature of 25° C. becomes 98.4% compared to the case at the device temperature of 20° C. Therefore, the corrected values of the electromagnetic wave intensity can be obtained by multiplying the respective values of the electromagnetic wave intensity measured at 25° C. by 1.016 (=100/98.4).

Figure 11:
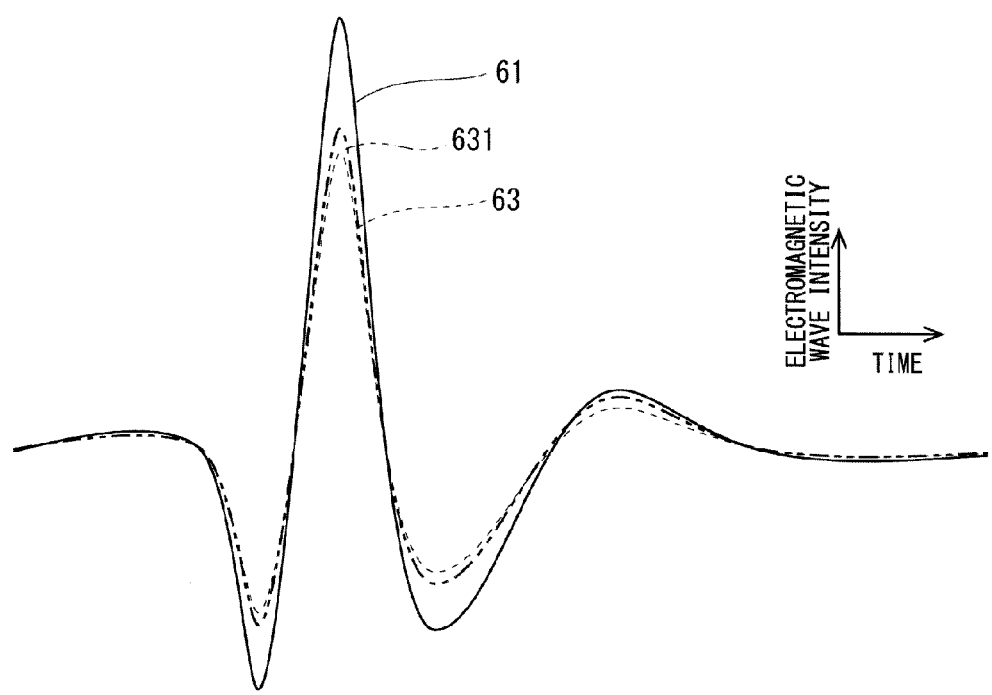
FIG. 11 is a diagram showing a temporal waveform after correction.

FIG. 11 is a diagram showing a temporal waveform 631 after correction. The temporal waveform 631 is the one obtained by correcting the temporal waveform 63. By correcting the electromagnetic wave intensity as described above, comparison under the same temperature condition is possible. In addition, the temporal waveform 631 is larger in peak value than the temporal waveform 63, so that the S/N ratio is improved.

Referring back to FIG. 7, after the correction process is completed, the electromagnetic wave intensity data are displayed on the monitor 17 (step S19 in FIG. 7). In detail, the data displayed on the monitor 17 include a temporal waveform restored from the electromagnetic wave intensity having been subjected to the correction process or an image (the electromagnetic wave intensity distribution image) produced by the imaging processing, based on the electromagnetic wave intensity having been subjected to the correction process.

The irradiation of the continuous light CW makes it possible to measure the solar cell panel 90 under condition close to the actually used condition. In this condition, the characteristics of the solar cell panel 90 can be more precisely inspected by suppressing the change in temperature of the solar cell panel 90 with the temperature changing part 31, and also by removing the components of the detected electromagnetic wave intensity caused by the device temperature fluctuations with the correction part 27. Furthermore, the inspection apparatus 100 can inspect the solar cell panel 90 at lower cost than the case of strictly controlling the temperature in the space in which the solar cell panel 90 is placed.

Incidentally, the Inspection Example 1 may be modified to detect the electromagnetic wave pulse LT1 by irradiation of the pulsed light LP11 while irradiating the solar cell panel 90 with the continuous light CW in the same manner as in the Inspection Example 2.

<2. Second Preferred Embodiment>

Figure 12:
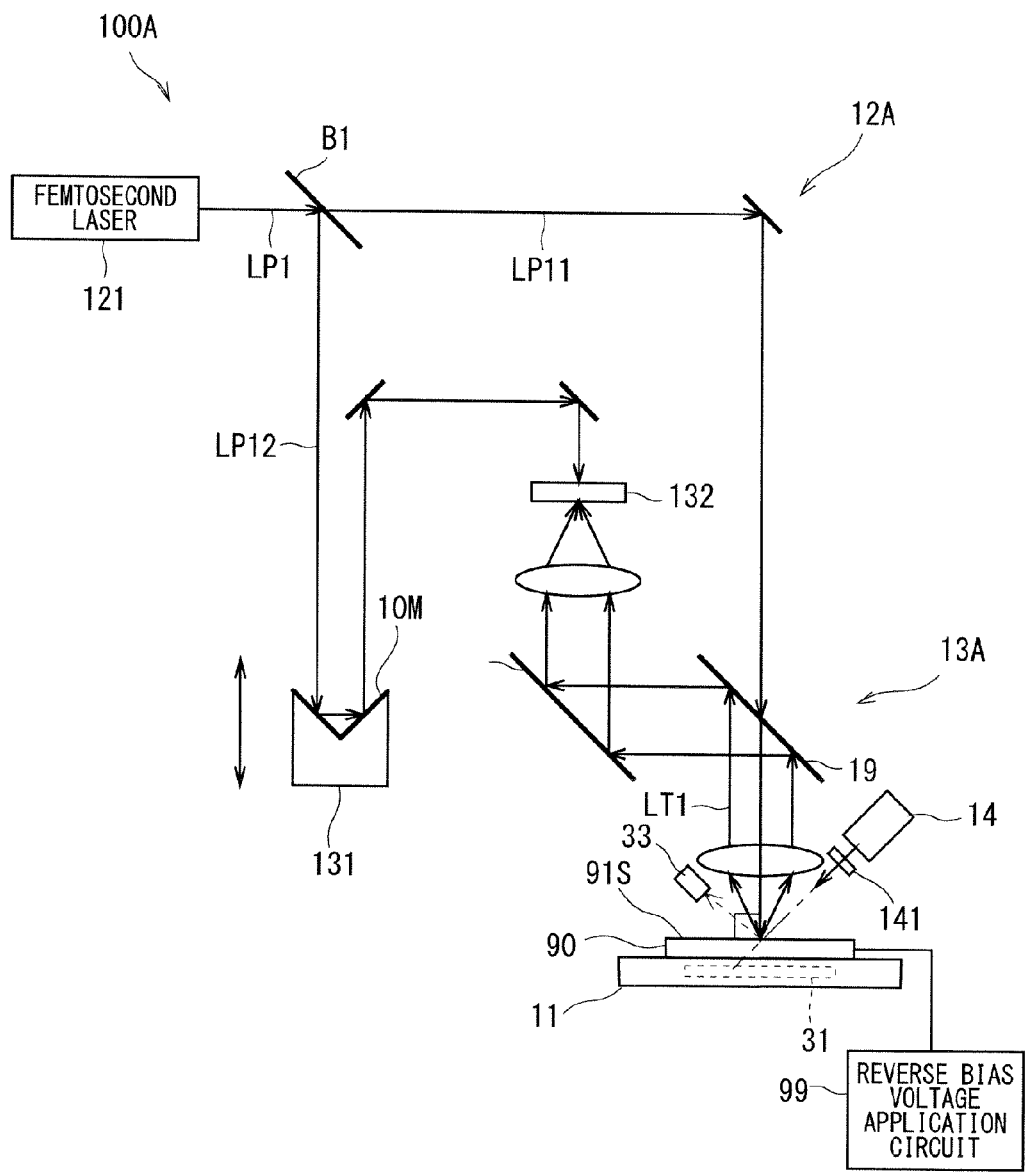
FIG. 12 is a schematic configuration diagram showing an irradiation part and a detection part included in an inspection apparatus according to a second preferred embodiment.

FIG. 12 is a schematic configuration diagram showing an excitation light irradiation part 12A and a detection part 13A included in an inspection apparatus 100A according to a second preferred embodiment. In the following description, the structural components having similar functions to those of the components of the inspection apparatus 100 according to the first preferred embodiment will be indicated by the same reference symbols, and description thereof will be omitted.

As shown in FIG. 12, in the inspection apparatus 100A, the pulsed light LP11 split by the beam splitter B1 transmits through the transparent conductive film substrate (ITO) 19, and perpendicularly enters the light receiving surface 91S of the solar cell panel 90. Then, among the electromagnetic wave pulses LT1 radiated from the solar cell panel 90 in response to the irradiation with the pulsed light LP11, the electromagnetic wave pulse LT1 radiated from the light receiving surface 91S side is reflected by the transparent conductive film substrate 19, and converged by a lens to enter the detector 132.

Similarly to the inspection apparatus 100 according to the first preferred embodiment, the inspection apparatus 100A also can detect the electromagnetic wave pulse LT1 radiated from the solar cell panel 90. In addition, the inspection considering the temperature dependent characteristics of the solar cell panel 90 can be performed by providing the temperature changing part 31 and the temperature measuring part 33.

<3. Third Preferred Embodiment>

FIG. 13 is a schematic configuration diagram showing an excitation light irradiation part 12B and a detection part 13B included in an inspection apparatus 100B according to a third preferred embodiment. In the inspection apparatus 100B, the pulsed light LP11 split by the beam splitter B1 perpendicularly enters the light receiving surface 91S of the solar cell panel 90. Then, among the electromagnetic wave pulses LT1 radiated from the solar cell panel 90 in response to the irradiation with the pulsed light LP11, the electromagnetic wave pulse LT1 radiated from (that is transmitted through) the back surface side of the solar cell panel 90 enters the detector 132 through the parabolic mirrors M1 and M2.

The inspection apparatus 100B also can detect the electromagnetic wave pulse LT1 radiated from the solar cell panel 90. In addition, the inspection considering the temperature dependent characteristics of the solar cell panel 90 can be performed by providing the temperature changing part 31 and the temperature measuring part 33.

<4. Fourth Preferred Embodiment>

Figure 14:
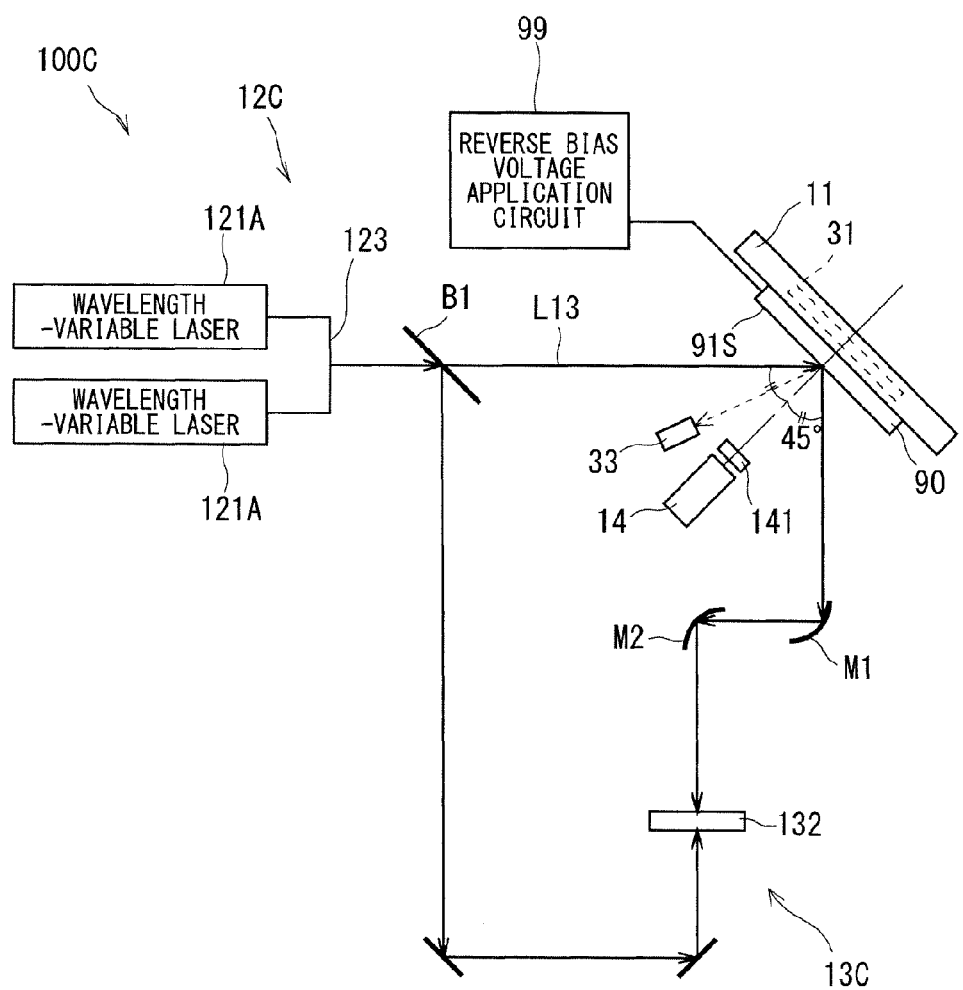
FIG. 14 is a schematic configuration diagram showing an irradiation part and a detection part included in an inspection apparatus according to a fourth preferred embodiment.

FIG. 14 is a schematic configuration diagram showing an excitation light irradiation part 12C and a detection part 13C included in an inspection apparatus 100C according to a fourth preferred embodiment. In the inspection apparatus 100C, two laser beams which are slightly different in oscillation frequency from each other are respectively outputted from a pair of wavelength-variable lasers 121A and 121A. Then, these laser beams are superposed by a coupler 123 made of an optical fiber, which is an optical waveguide, to produce an optical beat signal corresponding to a difference frequency. The difference frequency can be arbitrarily adjusted by making the oscillation frequency of the wavelength-variable laser 121A to be variable. The wavelength-variable laser 121A may, for example, be a distributed feedback (DFB) laser, which is possible to change the wavelength of its output laser beam almost continuously (for example, in steps of 2 nm) by temperature control.

The wavelength of the laser beam outputted from each of the wavelength-variable lasers 121A and 121A may, for example, be in the range of 300 nm (nanometers) to 2 μm (micrometers), and may be appropriately set depending on the width of the band gap of the photoelectric device to be inspected.

When laser beams having wavelengths 779 nm and 781 nm are outputted from the two wavelength-variable lasers 121A and 121A, for example, an optical beat signal of 1 THz, which is a difference frequency of these, can be produced by the coupler 123. Then, when the mixed light L13 is applied to the solar cell panel 90, which is an object to be inspected, photoexcited carriers are generated in the photoexcited carrier generating region, and accelerated by the internal electric field, so that an electromagnetic wave (a terahertz wave) corresponding to the frequency of the optical beat signal is radiated.

On the other hand, the mixed light L13 split by the beam splitter B1 is guided to be incident through mirrors to the detector 132 configured by a photoconductive switch (a photoconductive antenna). The detector 132 detects the electromagnetic wave in synchronization with the frequency of the optical beat signal contained in the entered mixed light L13. When the electromagnetic wave enters the detector 132, an electric current corresponding to the electric field strength of the electromagnetic wave is generated, and the quantity of the electric current is converted to a digital quantity through an I/V conversion circuit and an A/D conversion circuit. In this manner, the detection part 13C detects the electric field strength of the electromagnetic wave radiated from the solar cell panel 90.

As describe above, the inspection apparatus 100C also can detect the electromagnetic wave radiated from the solar cell panel 90. In addition, the inspection considering the temperature dependent characteristics of the solar cell panel 90 can be performed by providing the temperature changing part 31 and the temperature measuring part 33.

Further, in the present preferred embodiment, the wavelength-variable laser 121A is used as the light source of the excitation light. However, a light source other than the laser light source may be used as long as it is capable of outputting continuous light.

While the invention has been shown and described in detail, the foregoing description is in all aspects illustrative and not restrictive. It is therefore understood that numerous modifications and variations can be devised without departing from the scope of the invention.

What is claimed is:

1. An inspection apparatus for inspecting a photoelectric device, the inspection apparatus comprising:
    an excitation light irradiation part for irradiating said photoelectric device with excitation light for causing said photoelectric device to radiate a terahertz wave;
    a detection part for detecting the terahertz wave radiated from said photoelectric device in response to irradiation with said excitation light;
    a temperature changing part for changing a temperature of said photoelectric device at a part irradiated with said excitation light;
    a storage part for storing temperature correlation information regarding a correlation between a temperature of said photoelectric device and an intensity of said terahertz wave radiated from said photoelectric device in response to irradiation with said excitation light,
    wherein said temperature correlation information is obtained by changing the temperature of said photoelectric device by said temperature changing part, and collecting intensities of said terahertz wave radiated from said photoelectric device at respective temperatures; and
    a correction part for correcting an intensity of said terahertz wave detected by said detection part based on a temperature of said photoelectric device obtained by a temperature measuring part and said temperature correlation information.

2. The inspection apparatus according to claim 1, further comprising the temperature measuring part for measuring a temperature of said photoelectric device at the part irradiated with said excitation light.

3. The inspection apparatus according to claim 1, further comprising a continuous light irradiation part for irradiating said photoelectric device with continuous light.

4. The inspection apparatus according to claim 1, further comprising:
- a scanning mechanism for scanning said photoelectric device with said excitation light;
- an image producing part for producing a terahertz wave intensity distribution image showing an intensity distribution of a terahertz wave radiated from said photoelectric device; and
- a display part for displaying said terahertz wave intensity distribution image.

5. An inspection method for inspecting a photoelectric device, the inspection method comprising the steps of:
- (a) irradiating said photoelectric device with excitation light;
- (b) detecting a terahertz wave radiated from said photoelectric device in response to irradiation with said excitation light in said step (a);
- (c) changing a temperature of said photoelectric device;
- (d) storing temperature correlation information regarding a correlation between a temperature of said photoelectric device and an intensity of said terahertz wave radiated from said photoelectric device in response to irradiation with said excitation light in said step (a),
- wherein said temperature correlation information is obtained by changing the temperature of said photoelectric device in said step (c) and collecting intensities of said terahertz wave radiated from said photoelectric device at respective temperatures; and
- (e) correcting an intensity of said terahertz wave detected in said step (b) based on a temperature of said photoelectric device and said temperature correlation information.

* * * * *